United States Patent
Rojanapanthu et al.

(10) Patent No.: US 7,135,164 B2
(45) Date of Patent: Nov. 14, 2006

(54) ANDROGRAPHIS PANICULATA GEL AS AN ADJUNCT IN THE TREATMENT OF PERIODONTITIS

(75) Inventors: Pleumchitt Rojanapanthu, Bangkok (TH); Wandee Gritsanapan, Bangkok (TH); Mullika Sirirat, Bangkok (TH); Cholticha Amornchat, Bangkok (TH)

(73) Assignee: Mahidol University, Nakompathom (TH)

( * ) Notice: Subject to any disclaimer, the term of this patent is extended or adjusted under 35 U.S.C. 154(b) by 427 days.

(21) Appl. No.: 10/290,941

(22) Filed: Nov. 8, 2002

(65) Prior Publication Data

US 2003/0091517 A1   May 15, 2003

(30) Foreign Application Priority Data

Nov. 9, 2001   (TH) .................................... 069579

(51) Int. Cl.
*A61K 8/26*   (2006.01)
*A61K 36/00*   (2006.01)
*A61K 65/00*   (2006.01)

(52) U.S. Cl. .................. 424/58; 424/725; 424/779
(58) Field of Classification Search ............... 424/58, 424/779, 725
See application file for complete search history.

(56) References Cited

U.S. PATENT DOCUMENTS

| | | | |
|---|---|---|---|
| 4,915,936 A * | 4/1990 | Patterson et al. | 424/49 |
| 5,262,164 A * | 11/1993 | Damani | 424/422 |
| 5,447,725 A * | 9/1995 | Damani et al. | 424/435 |
| 6,071,524 A * | 6/2000 | Ribier et al. | 424/401 |
| 6,365,131 B1 * | 4/2002 | Doshi et al. | 424/49 |
| 6,576,662 B1 * | 6/2003 | Nanduri et al. | 514/473 |

FOREIGN PATENT DOCUMENTS

| | | | |
|---|---|---|---|
| JP | 403209313 A | * | 10/1991 |
| JP | 409157144 A | * | 6/1997 |
| JP | 02001247469 A | * | 10/2001 |
| WO | WO009101742 A1 | * | 2/1991 |

OTHER PUBLICATIONS

Rassameemasmaung, Supanee et al. "Subgingival Administration of Andrographis Paniculata Gel as an Adjunct in the Treatment of Adult Periodontitis" Department of Oral Medicine and Periodontics, Faculty of Dentistry, Mahidol University, Bangkok, Thailand. vol. 5 No. 1 1998, pp. 9-15.

Atsawasuwan, Phimon et al. "Subgingival Administration of Andrographis Paniculata Gel and Metronidaxole Gel as an Adjunct in the Treatment of Adult Periodontitis: Clinical and Microbiological Effects." Department of Hospital Dentistry, Gaculty of Dentistry, Mahidol University, Bangkok, Thailand. vol. 5 No. 2 1998, pp. 97-101.

* cited by examiner

Primary Examiner—Christopher R Tate
Assistant Examiner—Randall Winston
(74) Attorney, Agent, or Firm—Merchant & Gould P.C.

(57) ABSTRACT

A composition in the form of a biodegradable gel, chip or ointment is provided, for adjunct treatment of periodontitis, comprising: (i) an antimicrobial extract having antimicrobial or antibacterial activity against periodontal pathogens, preferably from one or more of the plants *Andrographis paniculata*, mangosteen (*Garcinia mangostana*) and turmeric (*Curcuma longa*); and (ii) a gel base containing a mixture of glyceryl monooleate and triglyceride. The composition is biodegradable, and forms a liquid crystal structure on contacting gingival fluid, which liquid crystal structure releases active ingredients gradually, to provide a sustained release dosage form.

11 Claims, No Drawings

ANDROGRAPHIS PANICULATA GEL AS AN ADJUNCT IN THE TREATMENT OF PERIODONTITIS

FIELD OF THE INVENTION

This invention relates to the use of a plant extract to provide a product useful as an adjunct for the treatment of periodontitis. This product is provided in a sustained release dosage form with a biocompatible and biodegradable carrier. The product is in a form of herb extract gel that changes its structure to liquid crystal when contacted with gingival fluid (gum lymph) in the periodontal pocket. The product may be packed in the special syringe with a blunt, curved needle for convenient loading in the periodontal pocket.

BACKGROUND OF THE INVENTION

At present it is reported that 90% of 40 year olds in the Thai population suffer from gingivitis, of which 80% can go on to develop to periodontitis when they are 60 years old. Patients have an inflammation of gingiva, alveolar bone, cementum and periodontal ligament, characterized by apical migration of the junctional epithelium, and loss of connective tissue attachment between the gingival fibre, periodontal ligament and cementum. There is resorption of the alveolar bone and development of pocket formation. If left untreated, the disease progresses to destruction of the supporting bone, whereby tooth mobility may be observed and sometimes periodontal abscess is found.

The basic treatment, from a patient's perspective, is oral hygiene instruction to control dental plaque and, from the dentist's perspective, is scaling and root planing. This procedure is not always sufficiently effective. This has led to the adjunctive use of antibiotics, usually in the form of a local delivery system rather than as a systemic antibiotic. Systemic antibiotics can cause side effects, for instance systemic metronidazole can irritate the gastrointestinal tract, and, in repeated doses, can affect the nervous system, skin and kidney. Alcohol consumption is not permitted during the period of taking this drug. In the case of systemic tetracycline, this must be used long-term, and in a high dose in order to maintain an effective concentration in the periodontal pocket. Consequently, the normal microorganism environment may be disturbed and super infected by fungus, and development of bacterial resistance strains may occur.

An early development of a local delivery system used a non-biodegradable carrier substance that had to be removed after the release of the antibiotic agent. This system had many disadvantages, as follows: initially, it was difficult to insert the drug into the periodontal pocket, and after complete release of the antibiotic agent, the patient had to return to see the dentist for removal of the carrier. The need to remove the carrier might be harmful to gingival healing and also irritating to the gum.

Recently, controlled local delivery systems using biodegradable substances have been developed to solve this problem. These contain antibiotic and, although they are beneficial, they are expensive. Products of this type are commercially available as Elysol®, containing metronidazole, or as an ointment containing minocycline. Both of these products may be packed in a special syringe and needle, ready for loading into the periodontal pocket.

DESCRIPTION OF THE INVENTION

According to the present invention, an antimicrobial extract is incorporated in a gel base to provide a gel, chip or ointment (hereinafter referred to as gel composition).

In a first aspect, a gel composition for adjunct treatment of periodontitis is provided, comprising:

(i) an antimicrobial extract having antimicrobial or antibacterial activity against periodontal pathogens, preferably from one or more of the plants *Andrographis paniculata*, mangosteen (*Garcinia mangostana*) and turmeric (*Curcuma longa*);

(ii) a gel base containing a mixture of glyceryl monooleate and triglyceride, wherein the composition forms a liquid crystal structure on contacting gingival fluid.

In a second aspect, a process of preparing a composition for use as an adjunct in the treatment of periodontitis is provided, comprising:

(i) preparing an antimicrobial extract having antimicrobial or antibacterial activity against periodontal pathogens, preferably from one or more of the plants *Andrographis paniculata*, mangosteen (*Garcinia mangostana*) and turmeric (*Curcuma longa*);

(ii) preparing a mixture of glyceryl monooleate and triglyceride as a gel base;

(iii) incorporating the antimicrobial extract into the gel base and mixing, to provide a composition that forms a liquid crystal structure on contacting gingival fluid.

The antimicrobial extract may be any plant extract containing antimicrobial or antibacterial active compounds effective against periodontal pathogens, e.g. against the bacterium *Porphyromonas gingivalis* that is known to cause periodontitis. The extract is preferably derived from *Andrographis paniculata*, a member of the plant family Acanthaceae, or from mangosteen (*Garcinia mangostana*) or turmeric (*Curcuma longa*) plants, which plants also contain antimicrobial or antibacterial active compounds effective against periodontal pathogens.

Preferably, the extract is derived from the plant *Andrographis paniculata*. Thus, the extract contains one or more of the following compounds: andrographolide (a diterpene lactone); deoxyandrographolide; 14-deoxy-11,12-didehydro-andrographolide; 14-deoxy-11-oxo-andrographolide; 14-deoxy-11-dehydro-andrographolide; andrographolide-19β-D glucoside; neoandrographolide; homo-andrographolide; andrographon; andrographan; andrographosterin; stigmasterol; peniculide.

The following procedure may suitably be used to prepare the antimicrobial extract:

Cleaned leaves and stem of *Andrographis paniculata* (Burmf.) Nees. are chopped into small pieces, dried in a hot air oven at 40–80° C. for 2–8 hours, then powdered and passed through a sieve with 1–4 mm pore size, and kept in a well sealed bottle.

The powder is extracted with organic solvents e.g. alcohol, acetone, chloroform, or other solvents, in a proportion of 400–700 grams of powders: 3,000–7,000 grams of solvent, with a Soxhlet apparatus at 30–95° C. for 3–80 hours.

Activated charcoal is added into the solvent extract (1–5 gram activated charcoal: 2–10 gram *Andrographis paniculata* extract), mixed and left for 1–5 hours in order to decolorize chlorophyll.

The mixture is filtered through a filter paper (Whatman no. 1), and the filtrate is concentrated by a rotary evaporator under reduced pressure at 30–95° C. The concentrated solution is then evaporated on a boiling water bath until a constant weight is attained, to provide the antimicrobial extract.

It will be appreciated that other suitable extraction methods, known to those skilled in the art, may instead be used in accordance with the invention, in order to prepare the antimicrobial extract. Leaves or other parts of the plants such as roots or rhizomes may be used, as appropriate, as raw material for extraction of the active ingredients. For *Andrographis paniculata* extract, preferably the leaves are used.

The gel base is prepared from a mixture of glyceryl monooleate and triglyceride. Glyceryl monooleate is commercially available, and may be prepared by reaction of oleic acid and glycerine in the presence of a suitable catalyst, to provide the monoglyceride ester of oleic acid and small amounts of other fatty acids. Thus, glyceryl monooleate is a mixture of the glyceride of oleic acid and other fatty acids, consisting mainly of the monoglyceride ester of oleic acid, with emollient property. Preferably, the glyceryl monooleate comprises at least 95 wt % monoglyceride ester of oleic acid.

Triglycerides include oils and fats, and are the main constituent of ordinary fat in foods. Triglycerides contain fatty acids, in the form of saturated fatty acids and/or unsaturated fatty acids, linked to a glycerol molecule.

The triglyceride used according to the present invention preferably is an oil, in particular a vegetable oil, for example, sesame oil, sunflower oil, soybean oil or safflower oil, or any mixture thereof.

The ratio of glyceryl monooleate: triglyceride is in the range from 2:1 to 10:1 by weight. The gel base mixture of glyceryl monooleate and triglyceride is incorporated in an amount of 60%–95%, by weight of the composition.

When glyceryl monooleate is contacted with water or the gingival exudates (gum lymph), it increases in viscosity and has a cubic mesophase structure. In combination with triglyceride, the cubic phase structure changes to hexagonal with the structure of liquid crystal. The liquid crystal structure can retain the active ingredient or the herb extract between the crystals, and releases the active ingredient content gradually, thus providing a sustained release dosage form.

The antimicrobial extract, preferably *Andrographis paniculata* extract, is incorporated, in an amount of 0.5%–30%, preferably 1–20%, more preferably 1%–15%, by weight of the composition (% based on dry extract). The concentration of extract used must, however, still be suitable for the gel base to be able to change to a liquid crystal structure.

An antioxidant or preservative agent is preferably incorporated in the composition, in a preferred amount of 0.5%–5%, by weight of the composition. A preferred antioxidant is D-α-tocopherol acetate.

Small amounts of auxiliary substances conventionally used in gel formulations may also be included, for example stabilizers, homogenising agents, texturising agents, soothing agents. For example, glycerin may assist in providing a homogeneous texture to the gel that is also soothing to the wound. Collagen may assist in healing of the wound. Preferably, glycerin or collagen, or both, are incorporated in the composition, preferably in a total amount of 0.1–5%, by weight of the composition.

The obtained gel is preferably packed in a syringe with the curved, blunt needle suitable for loading the gel into the periodontal pocket. Other convenient packaging can be used.

EXAMPLES

Example 1

1. Extraction of *Andrographis paniculata* Plant:

1.1 Cleaned leaves and stem of *Andrographis paniculata* (Burmf.) Nees. were chopped into small pieces, dried in a hot air oven at 60° C. for 5 hours, then powdered and passed through a sieve with 3 mm pore size, and kept in a well sealed bottle.

1.2 The powders were extracted with alcohol as solvent, in a proportion of 550 grams of powders: 5,000 grams of solvent, with a Soxhlet apparatus at 65° C. for 40 hours.

1.3 Activated charcoal was added into the solvent extract (3 gram activated charcoal: 6 gram *Andrographis paniculata* extract), mixed and left for 3 hours for decolorizing of chlorophyll.

1.4 The mixture was filtered through a filter paper (Whatman no. 1), and the filtrate was is concentrated by a rotary evaporator under reduced pressure at 65° C. The concentrated solution was then evaporated on a boiling water bath until a constant weight was attained.

2. Preparation of Compositions for Adjunct in the Treatment of Periodontitis:

2.1 Preparation of Gel Base:

Glyceryl monooleate, containing the glyceride of oleic acid and other fatty acids, and triglyceride (sesame oil) were mixed in a ratio of glyceryl monooleate: triglyceride of 6:1, by weight.

2.2 Incorporation of *Andrographis paniculata* Extract Into the Gel:

To the gel base mixture were added D-α-tocopherol acetate, as antioxidant; glycerin; and *Andrographis paniculata* extract, and mixed thoroughly to provide a gel composition containing 76.5% glyceryl monooleate/triglyceride gel base mixture, 20% *Andrographis paniculata* extract, 2.5% D-α-tocopherol acetate, and 1% glycerin, by weight of the composition.

3. Clinical Comparison Studies:

In a clinical comparison study with Elysol® (metronidazole gel), the results show that the percentage of black pigmented colonies (anaerobic microorganisms that cause periodontitis) had significantly reduced in the case of using the *Andrographis paniculata* gel but no reduction was found in the case of using the metronidazole gel.

In a clinical comparison study with minocycline ointment, the results showed that the *Andrographis paniculata* gel significantly reduced the percentage of motile rod shaped microorganisms compared with groups treated with the minocycline ointment and control groups.

The gel was found to have a liquid crystal structure after being contacted with gingival fluid.

Example 2

Using the same procedure and amounts as described in Example 1, a mangosteen extract was prepared by alcoholic extraction, and was incorporated into a gel base mixture of glyceryl monooleate and triglyceride (sesame oil) in a ratio of glyceryl monooleate: triglyceride of 6:1, by weight, together with D-α-tocopherol acetate as antioxidant, and glycerin. The mangosteen gel composition contained 76.5% glyceryl monooleate/triglyceride gel base mixture, 20% mangosteen extract, 2.5% D-α-tocopherol acetate, and 1% glycerin, by weight of the composition.

The gel formed a liquid crystal structure when contacted with water. Preliminary tests showed that the mangosteen gel was effective in reducing the percentage of microorganisms that cause periodontitis compared with control groups.

Example 3

Using the same procedure and amounts as described in Example 1, a turmeric extract was prepared by alcoholic extraction, and was incorporated into a gel base mixture of glyceryl monooleate and triglyceride (sesame oil) in a ratio of glyceryl monooleate: triglyceride of 6:1, by weight, together with D-α-tocopherol acetate as antioxidant, and glycerin. The turmeric gel composition contained 76.5% glyceryl monooleate/triglyceride gel base mixture, 20% turmeric extract, 2.5% D-α-tocopherol acetate, and 1% glycerin, by weight of the composition.

The gel formed a liquid crystal structure when contacted with water. Preliminary tests showed that the turmeric gel was effective in reducing the percentage of microorganisms that cause periodontitis compared with control groups.

The invention claimed is:

1. A gel composition for adjunct treatment of periodontitis, comprising:
   (i) antimicrobial extract obtained from *Andrographis paniculata* comprising andrographolide, deaxyandrographolide, 14-deoxy-11,12-didehydro-andrographolide, 14-deoxy-11-oxo-andographolide, 14-deoxy-11-dehydro-andrographolide, andographolide-19β-D glunoside, neoandrographolide, homo-andrographolide, andrographon, andrographan, andrographosterin, stimasterol, and peniculide, wherein the antimicrobial extract has antimicrobial or antibacterial activity against periodontal pathogens; and
   (ii) a gel base comprising a mixture of glyceryl monooleate and triglyceride;
   wherein the composition fonns a liquid crystal structure on contacting gingival fluid.

2. A composition according to claim 1, wherein the weight ratio of glyceryl monooleate: triglyceride is in the range of 2:1 to 10:1.

3. A composition according to claim 1, comprising the antimicrobial extract in an amount of 1%–15% by weight of the composition.

4. A composition according to claim 1, comprising the glyceryl monooleate and triglyceride mixture in an amount 80%–99% by weight of the composition.

5. A composition according to claim 1, wherein the composition is a sustained release gel, chip or ointment that is biodegradable.

6. A composition according to claim 1, wherein the triglyceride is one or more vegetable oils selected from sesame oil, sunflower oil, soybean oil and safflower oil.

7. A composition according to claim 1, further comprising an antioxidant or preservative agent.

8. A composition according to claim 7, comprising a D-αtocopherol acetate in an amount of 0.5%–5% by weight of the composition, as an antioxidant.

9. A composition according to claim 1, further comprising glycerin or collagen, or both.

10. A composition according to claim 9, comprising glycerin in an amount of 0.1%–5% by weight of the composition.

11. A composition according to claim 1, where the antimicrobial extract is from the leaves of *Andrographis paniculate*.

* * * * *